United States Patent [19]

Amschler et al.

[11] 4,131,678

[45] Dec. 26, 1978

[54] URAPIDIL/FUROSEMIDE COMPOUNDS, COMPOSITIONS AND USE

[75] Inventors: Hermann Amschler, Radolfzell; Kurt Klemm, Allensbach; Gerhard Ludwig, Constance, all of Germany

[73] Assignee: BYK Gulden Lomberg Chemische Fabrik GmbH, Constance, Germany

[21] Appl. No.: 767,214

[22] Filed: Feb. 9, 1977

[30] Foreign Application Priority Data

Feb. 9, 1976 [LU]  Luxembourg ............................ 74319

[51] Int. Cl.² .................... A61K 31/505; C07D 405/00
[52] U.S. Cl. ...................................... 424/251; 544/295; 260/347.2
[58] Field of Search ................. 260/256.4 C; 424/251; 544/295

[56] References Cited

U.S. PATENT DOCUMENTS

| | | | |
|---|---|---|---|
| 3,058,882 | 10/1962 | Stürm et al. | 260/239.6 |
| 3,957,786 | 5/1976 | Klemm et al. | 260/256.4 C |

*Primary Examiner*—Jose Tovar
*Assistant Examiner*—James H. Turnipseed
*Attorney, Agent, or Firm*—Berman, Aisenberg & Platt

[57] ABSTRACT

A combination of urapidil and furosemide, e.g., in the form of an acid-addition salt, in the form of a physical admixture or in the form of two distinct components collectively constitutes an effective active ingredient in the treatment of hypertension. The combination is advantageously incorporated in a standard dosage form and administered by various routes to mammals afflicted with high blood pressure. By combining furosemide with urapidil on one of the noted forms, the maximum hypotensive activity of urapidil is increased, while the side effects and toxicity of urapidil are reduced.

15 Claims, No Drawings

URAPIDIL/FUROSEMIDE COMPOUNDS, COMPOSITIONS AND USE

BACKGROUND

USP 3,957,786 (corresponding to German Specification 1,942,405) concerns piperazinylalkylaminouracils (and their salts with inorganic or organic acids) which exhibit hypotensive activity superior to that of previously-known antihypertensive agents. Of the compounds actually named therein, exploratory clinical testing established that the title compound of Example 4, 1,3-dimethyl-4-($\gamma$-[4-(o-methoxyphenyl)-piperazinyl(1)]-propylamino)uracil (urapidil), is particularly well suited for treating hypertension. However, further testing revealed that urapidil therapy achieved blood-pressure normalization in only about half of the patients with essential and secondary hypertension (of different degrees of gravity) to whom it was administered. At the same time, the compatibility of this hypotensive agent failed to fulfil all expectations. A product yielding a higher rate of blood-pressure normalization is required for wide therapeutic application.

SUMMARY OF THE INVENTION

By combining furosemide with urapidil, the maximum hypotensive activity of urapidil is increased and the side effects and toxicity of urapidil are reduced in addition to increasing the incidence of blood-pressure normalization of mammals afflicted with hypertension and to whom urapidil is administered. The combined product constitutes a hypotensive agent which is effective and compatible for wide therapeutic application.

The combination of furosemide with urapidil is optionally a chemical combination (e.g. in the form of an acid-addition salt) and/or a physical combination (in the form of an admixture or two distinct and separate components). If the urapidil is in the form of a physical combination with furosemide, it is optionally in the form of a pharmacologically-acceptable acid-addition salt with an appropriate (organic or inorganic) acid. Such acids are well known and are exemplified in the noted patent (cf. column 8, first complete paragraph), the entire disclosure of which is incorporated herein by reference. A preferred example is the hydrochloride.

If the furosemide is in the form of a physical combination with urapidil, it is optionally in the form of a compatible and physiologically-acceptable salt (such as an alkali-metal, e.g. sodium or potassium, or ammonium salt) with a suitable base. Irrespective of the precise form of urapidil and/or furosemide in the combination of the two, the relevant equivalent amounts of the respective components of the combination is controlling over the enhancement of the hypotensive effect of urapidil imparted to it by the furosemide combined therewith.

Whatever the form of the combination of furosemide with urapidil, such combination is useful as a hypotensive agent. It is preferably administered orally in virtually any of the dosage forms suitable for such mode of administration. The combination is readily formulated into medicaments as the "active ingredient" thereof. When medicament compositions are so formulated, they contain an effective concentration of the noted combination for the route of administration for which the provided dosage form is designed.

DETAILS

The "active ingredient" upon which the subject invention is based is a chemical and/or physical combination of urapidil with furosemide. The chemical combination is the 1:1 acid-addition salt combining one mole of urapidil with one mole of furosemide.

Even when the urapidil/furosemide acid-addition salt is employed, it is optionally physically combined with additional urapidil(or a pharmacologically-acceptable acid-addition salt thereof) and/or furosemide(or a physiologically-acceptable salt thereof).

Physical combinations include all admixtures as well as forms in which the essential components are separate and distinct. An example of the latter is a dosage form in which one component is in a substrate and the other is in a coating on the substrate. This type of dosage form is known and is prepared from the subject components in essentially the same manner as from other active ingredients.

Preferred combinations are those which contain the respective components of the active ingredient in a molar ratio of urapidil:furosemide in the range of from 5:1 to 1:5. Of these combinations, those having a ratio of such components in the range of from 3:1 to 1:3 are of particular interest, and those in which the ratio is 1:1 are outstandingly important.

The invention also relates to a method for treating hypertension in mammals, particularly in humans, which comprises administering a therapeutically-effective amount of the active ingredient according to the invention or of a medicament containing the active ingredient to a living organism, e.g. a male or female patient, afflicted with high blood pressure.

Such medicament, formulated according to processes known to those skilled in the art, is optionally in any standard dosage form suitable for a recognized mode of administration. It is preferably administered orally or parenterally injected, e.g., subcutaneously, intramuscularly or intravenously. Pharmaceutical preparations based on the active ingredient are advantageously in unit dosage form adapted for the desired mode of administration. A unit dose is, e.g. a tablet, a capsule or a measured volume amount of a powder, a granulate or a solution. "Unit dose", in the sense of the present invention, is a physically-specified unit which contains an individual amount of active ingredient (combination of urapidil with furosemide) in admixture with a pharmaceutical diluent therefor or together with a pharmaceutical excipient. The amount of active ingredient is selected so that one or more units are usually enough for an individual therapeutic administration.

The unit dose, however, is optionally subdivisible, e.g. in the case of tablets provided with grooves, when only a fraction, such as a half or a quarter, of the subdivisible unit is needed for a single therapeutic administration.

Pharmaceutical preparations according to the invention contain, when they are present in unit dosage form, a total of from 5 to 150, advantageously from about 25 to 100 and, in particular, from about 40 to 70, milligrams (mg) of active ingredient. Therapeutic administration of such pharmaceutical preparations is effected 1 or several, e.g. three, times daily, e.g. after each meal and/or in the evening. Administration may, however, particularly in the case of application as a maintenance dose, be effected only on every second day.

The actual dose administered is governed by the frequency of administration, by the duration of treatment, by the nature and gravity of the illness and by the weight, age and state of health of the subject. In general, the daily (oral) dose for mammals, e.g. humans, lies between about 0.1 and 1.0 mg of active ingredient per kilogram (kg) of body weight.

the pharmaceutical preparations generally comprise active ingredient according to the invention and non-toxic, pharmaceutially-acceptable medicament excipient (used as additive in solid, semi-solid or liquid form or as surrounding agent, for example in the form of a capsule, a tablet coating, a bag or other container for the therapeutically-active constituent). An excipient optionally serves, e.g., as intermediary for the uptake of the medicament by the body, as formulation auxiliary, as sweetener, as flavoring, as coloring matter or as preservative.

Oral dosage forms include tablets, dragées, hard and soft capsules (e.g. of gelatin), dispersible powders, granulates, aqueous and oily suspensions, emulsions, solutions and syrups.

Tablets contain inert diluents, e.g. calcium carbonate, calcium phosphate, sodium phosphate or lactose; granulating or distributing agent, e.g. maize starch or alginate; binder, e.g. starch, gelatin or acacia gum; and/or lubricant, e.g. aluminum or magnesium stearate, talc or silicone oil. They are optionally additionally provided with a coating which, e.g., is of such a nature that it causes delayed dissolving and resorption of the medicament in the gastro-intestinal tract and thus, e.g., better compatibility or an extended duration of action. Gelatin capsules contain, e.g., the active ingredient in admixture with a solid diluent, e.g. calcium carbonate or kaolin, or an oily diluent, e.g. olive oil, arachis oil or paraffin oil.

Illustrative suspending agents are, e.g., sodium carboxymethylcellulose, methylcellulose, hydroxypropylcellulose, sodium alginate, polyvinylpyrrolidone, gum tragacanth and acacia gum; dispersing and wetting agents include, e.g., polyoxyethylene stearate, heptadecaethyleneoxycetanol, polyoxyethylenesorbitol mono-oleate, polyoxyethylenesorbitan mono-oleate and lecithin; preservatives comprise, e.g., methyl or propyl hydroxybenzoates; sucrose, lactose, dextrose and invert sugar syrup are typical of flavoring and sweetener.

Oily suspensions contain, e.g., arachis oil, olive oil, sesame oil, coconut oil or paraffin oil and thickener, such as beeswax, hard paraffin or cetyl alcohol, in addition to sweetener, flavoring and antioxidant.

Powders and granulates which are dispersible in water optionally contain the active ingredient in admixture with dispersing, wetting and suspending agents, e.g. those previously mentioned, as well as with sweetener, flavoring and coloring matter.

Emulsions contain, e.g., olive oil, arachis oil or paraffin oil besides emulsifier, such as acacia gum, gum tragacanth, phosphatide, sorbitan mono-oleate, polyoxyethylenesorbitan mono-oleate, and sweetener and flavoring.

The different dosage forms are prepared according to well-established procedures by substituting the instant active ingredient in the desired amount for that in corresponding medicament compositions based on other active ingredients having similar or different pharmacological activity.

Parenterally, the medicaments are administered as sterile solutions, e.g., isotonic salt solutions comprising dispersing and/or wetting agents and/or pharmacologically compatible diluting agents, as for example kollidon. They are optionally bottled in the form of continuous intravenous drip bottles for continuous intravenous administration.

The active ingredient and medicament containing same (according to the invention) are very well suited for therapeutic application. Exploratory tests on male and female patients with hypertension (varying in origin and differing in degree of gravity) resulted in normalizing blood pressure in the majority of hypertensive persons to which the active ingredient was administered. Further, superiority (compared to urapidil) of medicament according to the invention was observed with regard to increased activity maximum, reduced side effects, e.g. urine excretion and electrolyte excretion, and reduced toxicity. The active ingredient and medicament according to the invention therefore represent a substantial advance in the treatment of hypertension.

The preparation of the active ingredient is effected according to processes which are known per se to one skilled in the art. For example, the 1:1 furosemide salt of urapidil is obtained by direct reaction of equimolar amounts of furosemide and urapidil dissolved in suitable solvents. Such solvents include aliphatic alcohols, such as methanol, ethanol and ethyl cellosolve; chlorinated hydrocarbons, such as methylene chloride and chloroform; aliphatic carboxylic acid amides or nitriles, such as dimethyl formamide, dimethyl acetamide and acetonitrile; aliphatic ketones, such as acetone and methyl ethyl ketone; or mixtures thereof.

The 1:1 urapidil/furosemide is, however, also obtained by resalting, e.g. by reaction of an appropriate urapidil salt, such as a hydrohalide, preferably the hydrochloride, with a suitable salt of furosemide, such as an alkali-metal salt, preferably the sodium salt, or the ammonium salt. The starting materials, dissolved in suitable solvents, are added to one another. Sufficient differences in solubility between the strating product and end product are essential, and the inorganic salt formed as a by-product, e.g. sodium chloride, should be readily separable. Suitable solvents for the resalting are, for example, water, lower aliphatic alcohols (such as methanol and ethanol), aliphatic ketones (such as acetone and methyl ethyl ketone), carboxylic acide amides or nitriles (such as dimethylformamide, dimethylacetamide and acetonitrile) or mixtures thereof with water.

By treating hypertension with a combination of urapidil and furosemide, a mode of treatment is provided which is sufficiently effective and compatible for wide therapeutic use. The invention relates to combinations (physical and/or chemical) of urapidil and furosemide, to medicaments (including pharmacologically-acceptable hypotensive compositions) containing such combinations and useful for reducing the blood pressure of mammals afflicted with hypertension and to a method of treating hypertension in mammals, particularly humans, by administering to a living afflicted organism, such as a male or female patient, a therapeutically-effective amount of such a combination or of a medicament containing same.

As a result of a synergistic effect of the essential components of the active ingredient on one another, the amount of active ingredient administered and, therefore, to be metabolized, i.e. the active ingredient loading of the patient, is greatly reduced. The medicament according to the invention therefore represents a substantial advance in the treatment of hypertension.

The following examples are entirely illustrative in nature and in no way limit the invention to which the appended claims are directed.

EXAMPLE 1

1,3-dimethyl-4-[3-(1-o-methoxyphenylpiperazinyl-4)-propylamino]uracil-[2-(2-furylmethyl)amino-4-chloro-5-sulfamylbenzoate] (salt)

Dissolve 584 g (1.5 moles) of hot (45° to 50° C) 1,3-dimethyl-4-(γ-[4-(o-methoxyphenyl)piperazinyl-(1)]-propylamino)uracil (urapidil) in 3 liters of methanol and 1 liter of chloroform and add thereto a hot (45° to 50° C) suspension of 500 g (1.5 moles) of 2-(2-furylmethyl)amino-4-chloro-5-sulfamylbenzoic acid (furosemide) in 1 liter of methanol. In a short time the resulting mixture forms a clear solution from which the title 1:1 acid-addition salt immediately begins to crystallize out. Draw off half of the solvent mixture in a vacuum; cool the remaining slurry of crystals for a further period on an ice-(sodium chloride) mixture and then suction filter it. Wet the residue with methanol and dry filter cake in a vacuum at 80° C to obtain, in this manner, 1,078.6 grams (g) of the title salt, m.p.: 219° C, corresponding to a yield of 99.5% of theory.

EXAMPLE 2

1,3-dimethyl-4-[3-(1-o-methoxyphenylpiperazinyl-4)-propylamino]uracil-[2-(2-furylmethyl)amino-4-chloro-5-sulfamylbenzoate] (salt)

Dissolve 331.7 g (1mole) of furosemide and 44 g (1.1 moles) of caustic soda in 3 liters of water, with heating. With constant stirring, add to this solution of solution of 387.5 g (1 mole) of urapidil in 550 milliliters (ml) of 2N hydrochloric acid and 2,150 ml of water. The title 1:1 acid-addition salt crystallizes out even during the mixing of the solutions. Cool the thus-obtained salt mixture to 0° C, suction filter the resulting slurry of crystals and wash the obtained filter cake several times with ice-cold water until the filtrate is chloride-free. Dry the product in a vacuum at 80° C to obtain 699.8 g of the title salt, m.p.: 219° C, corresponding to a yield of 97.3% of theory.

EXAMPLE 3

Tablets with 50 mg of salt

Production of a batch of 100,000 tablets, each of 50 milligrams (mg) of salt:

| | |
|---|---|
| 1. salt | 5.0 kg |
| 2. maize starch | 8.2 kg |
| 3. lactose | 4.8 kg |
| 4. highly-disperse silicic acid | 0.3 kg |
| 5. sodium lauryl sulfate | 0.4 kg |
| 6. gelatin | 0.5 kg |
| 7. glycerin | 0.1 kg |
| 8. talc | 0.5 kg |
| 9. magnesium stearate | 0.2 kg |
| | 20.0 kg |

Mix and finely grind 1 and 3. Mix the resulting admixture with 4, 5 and 7 kilograms (kg) of 2. Moisten the thus-obtained powder mixture with a solution of 6 and 7 in 7 liters of water and then pass it through a sieve of mesh size 1.25 millimeter (mm). Dry and then mix the resulting granulate well with the remainder of 2, 8 and 9 before compressing it into tablets, each of 200 mg.

EXAMPLE 4

Dragées with 25 mg of salt

Production of a batch of 400,00 varnished tablets:

| | |
|---|---|
| 1. salt | 10.0 kg |
| 2. lactose | 32.0 kg |
| 3. potato starch | 8.0 kg |
| 4. polyvinylpyrrolidone | 2.8 kg |
| 5. polyethyleneglycol 4000 | 2.0 kg |
| 6. talc | 1.6 kg |
| 7. magnesium stearate | 0.8 kg |
| 8. Primojel | 2.8 kg |
| | 60.0 kg |

Mix 1 with 2 and 3 and then sieve the obtained powder mixture. Dissolve 4 and 5 in 6 liters of ethanol and 4 liters of water. Moisten the powder mixture with this solution and then pass it through a sieve of mesh size 1.25 mm. Dry and then mix the resulting granulate with 6, 7 and 8 before compressing the prepared admixture into dragée cores, each of 150 mg. Coat these cores in a coating pan with the following suspension:

| | |
|---|---|
| 1. methylcellulose | 1.8 kg |
| 2. shellac | 0.3 kg |
| 3. polyvinylpyrrolidone | 0.3 kg |
| 4. polyethyleneglycol 4000 | 0.01 kg |
| 5. titanium dioxide | 0.29 kg |
| 6. amaranth red | 0.3 kg |
| 7. isopropanol | 10 liters |
| 8. methylene chloride | 10 liters |

EXAMPLE 5

Capsules with 30 mg of salt

Production of a batch of 100,000 capsules:

| | |
|---|---|
| 1. salt | 3.0 kg |
| 2. lactose | 4.2 kg |
| 3. Primojel | 1.5 kg |
| 4. Kollidon | 0.3 kg |

Carefully mix and finely grind 1,2 and 3. Dissolve 4 in 3 liters of water. Moisten the ground powder mixture with this solution and pass it through a sieve of 1.25 mm mesh size. Dry the resulting granulate and then fill size 4 capsules with 90 mg (each) of such granulate.

EXAMPLE 6

Tablets with 50 mg of combination

Production of a batch of 100,000 tablets

| | |
|---|---|
| 1. urapidil | 2.7 kg |
| 2. furosemide | 2.3 kg |
| 3. maize starch | 8.2 kg |
| 4. lactose | 4.8 kg |
| 5. highly-disperse silicic acid | 0.3 kg |
| 6. sodium lauryl sulfate | 0.4 kg |
| 7. gelatin | 0.5 kg |
| 8. glycerin | 0.1 kg |
| 9. talc | 0.5 kg |
| 10. magnesium stearate | 0.2 kg |

Mix and finely grind 1, 2 and 4. Mix this mixture with 5, 6 and 7 kg of 3. Moisten the resulting powder mixture with a solution of 7 and 8 in 7 liters of water and pass it through a sieve of mesh size 1.25 mm. Dry the thus-obtained granulate before mixing it well with the remainder of 3, 9 and 10 and compressing the resultant into tablets, each of 200 mg.

EXAMPLE 7

Dragées with 50 mg of combination

Production of a batch of 400,000 varnished tablets:

| | | |
|---|---|---|
| 1. | urapidil | 15.56 kg |
| 2. | furosemide | 4.44 kg |
| 3. | lactose | 22.00 kg |
| 4. | potato starch | 8.00 kg |
| 5. | polyvinylpyrrolidone | 2.80 kg |
| 6. | polyethyleneglycol 4000 | 2.00 kg |
| 7. | talc | 1.60 kg |
| 8. | magnesium stearate | 0.80 kg |
| 9. | Primojel | 2.80 kg |
| | | 60.00 kg |

Mix 1 and 2 with 3 and 4 and then sieve the resulting powder mixture. Dissolve 5 and 6 in 6 liters of ethanol and 4 liters of water. Moisten the powder mixture with this solution and pass it through a sieve of mesh size 1.25 mm. Dry the thus-obtained granulate before mixing it with 7, 8 and 9. Compress the resultant into dragée cores, each of 150 mg, and coat them in a coating pan with the following suspension:

| | | |
|---|---|---|
| 1. | methylcellulose | 1.8 kg |
| 2. | shellac | 0.3 kg |
| 3. | polyvinylpyrrolidone | 0.3 kg |
| 4. | polyethyleneglycol 4000 | 0.01 kg |
| 5. | titanium dioxide | 0.29 kg |
| 6. | isopropanol | 10 liters |
| 7. | methylene chloride | 10 liters |

EXAMPLE 8

Tablets with 50 mg of combination

Production of a batch of 100,000 tablets:

| | | |
|---|---|---|
| 1. | urapidil | 1.4 kg |
| 2. | furosemide | 3.6 kg |
| 3. | potato starch | 10.3 kg |
| 4. | polyvinylpyrrolidone (average molecular weight 25,000) | 0.5 kg |
| 5. | carboxymethylcellulose | 1.8 kg |
| 6. | magnesium stearate | 0.2 kg |
| 7. | talc | 4.5 kg |
| | | 22.3 kg |

Spray the weighed amounts of 1, 2 and 3 (in a GLATT fluidized-bed granulator) with a solution of 4 in 5 liters of water. After drying to a relative moisture content of from 50 to 60%, add constituents 5 and 6 thereto and homogeneously mix. After sieving, compress the resulting granulate into tablets, each of 223 mg and having an 8 mm diameter.

EXAMPLE 9

Capsules with 30 mg of combination

Production of a batch of 100,000 capsules:

| | | |
|---|---|---|
| 1. | urapidil | 1.62 kg |
| 2. | furosemide | 1.38 kg |
| 3. | lactose | 4.2 kg |
| 4. | Primojel | 1.5 kg |
| 5. | Kollidon | 0.3 kg |
| | | 9.0 kg |

Carefully mix and finely grind 1, 2, 3, and 4 to produce a powder mixture. Dissolve 5 in 3 liters of water. Moisten the powder mixture with this solution and pass it through a sieve of mesh size 1.25 mm. Dry the resulting granulate and then fill size 4 capsules with 90 mg (each) of such granulate.

The following pharmacological data verify the superiority of the salt according to the invention and the superiority of the combinations according to the invention over the individual components.

For the determination of the antihypertensive action, the compounds or mixtures are administered daily, by means of oesophageal sound, in the stated doses on the stated number of consecutive days, to, in each case, eight rats (OKAMOTO strain) with genetically caused hypertension. The measurement of the blood pressure was effected, in each case, 2, 6 and 24 hours after administration of the substance.

The measurement of the systolic blood pressure was effected with the aid of an inflatable cuff place around the tail root, on which cuff there are arranged distally annularly 3 piezoelectric crystals (at a distance of 120°) for registering the pulse waves. The determination of the blood pressure was effected by inflation of the cuff and graphic recording of the pulse amplitude.

The animals were kept in, and the experiments were carried out in, an ambience of 26° C and an atmospheric humidity of 60%. To accustom them to the measuring process, the animals were habituated to the measuring process 2 - 3 times daily for three days. For this purpose, as in the following experiments, the rats were put into tunnel-shaped wire cage; one narrow side of the cages is slidable, the other has an opening for the taking through of the tail. In order to ensure a blood flow through the tail artery during the measurement, the tails are irradiated for 5 - 10 minutes with a red-light lamp (150 watts) (distance: animal — lamp = 50 cm). Air temperature in the immediate region of the tail was 30 - 33° C. The body of the animals is protected from direct irradiation by plastic disks which are arranged about 10 cm above the cages.

From Table 1, in which the influence of urapidil, furosemide and of the salt on the systolic blood pressure of genetically hypertonic rats is compiled, it is seen that the salt according to the invention has an excellent antihypertensive action with a dose at which the component urapidil, exhibits only a slight effect and the component, furosemide, exhibits no effect. The salt exhibits, according to Table 1, a synergistic, i.e. a super-additive, action compared to that of the individual constituents.

From Table 2 it is seen that the combinations, according to the invention, of urapidil with furosemide exhibit an excellent antihypertensive action with doses at which the individual components have little or no effect. From the Table it emerges unambiguously that furosemide exerts a synergistic effect on the hypotensive action of urapidil. In the case of combinations of practically ineffective doses of urapidil or furosemide, an antihypertensive effect is obtained which is more pronounced than that of larger amounts of urapidil alone.

The combinations have the advantage that they — because of their reduced doses of urapidil — do not show the side effects of urapidil, e.g. sedation, but do exert a pronounced antihypertensive action.

Table 1

Influence of urapidil, furosemide and salt* on the systolic blood pressure of genetically hypertonic rats

| Substance | Dose** mg/kg | Urapidil proportion mg/kg | Furosemide proportion mg/kg | Days administered | Average blood pressure SV*** | Average change**** of blood pressure (mm Hg) after | | |
|---|---|---|---|---|---|---|---|---|
| | | | | | | 2 hrs. | 6 hrs. | 24 hrs. |
| Salt* | 10 | 5.4 | 4.6 | 4 | 197 | −31 | −30 | −6 |
| Furosemide | 9.2 | 0 | 9.2 | 14 | 190 | +1 | −4 | +4 |
| Urapidil | 10 | 10 | 0 | 8 | 206 | −17 | −15 | −6 |

*Salt: compound according to Example 1
**daily administration of a single dose
***SV: starting values (mm Hg)
****calculated by summing up the values obtained after the indicated hours after each administration and dividing the sum by the days of administration

Table 2

Influence of urapidil, furosemide and their combinations on the systolic blood pressure of genetically hypertonic rates

| Substance or combination | Dose* mg/kg | Urapidil proportion mg/kg | Furosemide proportion mg/kg | Days administered | Average blood pressure SV** | Average change*** of blood pressure (mm Hg) after | | |
|---|---|---|---|---|---|---|---|---|
| | | | | | | 2 hrs. | 6 hrs. | 24 hrs. |
| Urapidil (U) | 10 | 10 | 0 | 8 | 206 | −17 | −15 | −6 |
| Furosemide (F) | 9.22 | 0 | 9.22 | 14 | 190 | +1 | −4 | +4 |
| U/F molar ratio 1:3 | 10 | 2.8 | 7.2 | 4 | 190 | −22 | −22 | −1 |
| U/F molar ratio 1:1 | 10 | 5.4 | 4.6 | 4 | 197 | −31 | −30 | −6 |
| U/F molar ratio 3:1 | 10 | 7.8 | 2.2 | 4 | 201 | −39 | −36 | −15 |

*daily administration of a single dose
**SV: starting values (mm/Hg)
***calculated by summing up the values obtained after the indicated hours after each administration and dividing the sum by the days of administration For the determination of the acute toxicity, the compounds and mixtures were suspended by ultrasonic methods in 1% strength solution of Tylose. Of the suspensions, in each case 40 ml/kg were administered to, in each case, 5 female albino mice (NMRI).

From Table 3, in which the lethal effect (in %) of urapidil and of the salt, in dependence on the dose, is reproduced, it is seen that the salt is substantially less toxic than urapidil. Thus, e.g. 5000 mg/kg of salt with a urapidil proportion of 2690 mg/kg have no lethal effect, whereas 1076 mg/kg of urapidil already cause a lethality of 80% and 1614 mg/kg of urapidil cause a lethality of 100%.

Table 3

Lethal effect of urapidil and of the salt of the formula I on the female albino mouse

| Substance | Dose total (mg/kg) | Urapidil proportion (mg/kg) | Furosemide proportion (mg/kg) | Lethality (%) |
|---|---|---|---|---|
| Urapidil | 538 | 538 | — | 0 |
| Salt(+) | 1000 | 538 | 462 | 0 |
| Urapidil | 1076 | 1076 | — | 80 |
| Salt(+) | 2000 | 1076 | 924 | 0 |
| Urapidil | 1614 | 1614 | — | 100 |
| Salt(+) | 3000 | 1614 | 1386 | 0 |
| Urapidil | 2152 | 2152 | — | 100 |
| Salt(+) | 4000 | 2152 | 1848 | 0 |
| Salt(+) | 5000 | 2690 | 2310 | 0 |

(+)Salt: compound according to Example 1

From Table 4, in which the lethal effect (in %) of urapidil and of a combination in the molar ratio 1:1 is reproduced, it can be seen that the combination is substantially less toxic than urapidil. Thus, the administration of 5000 mg/kg of the 1:1 combination (urapidil proportion 2690 mg/kg) leads to no death (lethality = 0%) whereas, when alone 1076 mg/kg of urapidil is administered, the lethality is already 80% and, with 1614 mg/kg of urapidil, the lethality is 100%.

Table 4

Lethal effect of urapidil and of its combination with the furosemide in the molar ratio 1:1 on the female albino mouse

| Substance | Dose total (mg/kg) | Urapidil proportion (mg/kg) | Furosemide proportion (mg/kg) | Lethality (%) |
|---|---|---|---|---|
| Urapidil | 538 | 538 | — | 0 |
| Combination | 1000 | 538 | 462 | 0 |
| Urapidil | 1076 | 1076 | — | 80 |
| Combination | 2000 | 1076 | 924 | 0 |
| Urapidil | 1614 | 1614 | — | 100 |
| Combination | 3000 | 1614 | 1386 | 0 |
| Urapidil | 2152 | 2152 | — | 100 |
| Combination | 4000 | 2152 | 1848 | 0 |
| Combination | 5000 | 2690 | 2310 | 0 |

From Table 5, in which the influence of urapidil-furosemide combinations with various furosemide content on the survival rate of female albino mice is reproduced, it can be seen that the toxicity of urapidil is considerably reduced by additions of furosemide. Whereas the survival rate with administration of 1500 mg/kg of urapidil on its own is zero, with constant proportion of urapidil the survival rate rises with increasing addition of furosemide. Already with a molar ratio of urapidil: furosemide of 5:1, the servival rate is 40%. The protective action of the furosemide manifests itself particularly clearly from a molar ratio of urapidil: furosemide of 3:1 onwards and reaches an optimum at a molar ratio of about 1:1.

Table 5

Influence of urapidil and its combinations with furosemide on the survival rate of female albino mice

| Urapidil dose (mg/kg) | Furosemide dose (mg/kg) | Molar ratio | Survival rate (%) |
|---|---|---|---|
| 1500 | — | — | 0 |
| 1500 | 180 | 7.1 : 1 | 0 |
| 1500 | 250 | 5.1 : 1 | 40 |
| 1500 | 360 | 3.6 : 1 | 60 |
| 1500 | 500 | 2.6 : 1 | 60 |
| 1500 | 720 | 1.8 : 1 | 80 |
| 1500 | 1000 | 1.3 : 1 | 100 |
| 1500 | 1200 | 1.1 : 1 | 100 |

The invention and its advantages are readily understood from the foregoing description, from which it is apparent that various changes may be made in the components of the active ingredient, in the form of the active ingredient, in medicament containing the active ingredient and in the manner and mode of administering the active ingredient and such medicament without departing from the spirit and scope of the invention or sacrificing its material advantages. The products, the combinations of ingredients, the compositions and the methods of use hereinbefore described are merely illustrative of preferred embodiments of the invention.

Throughout the disclosure reference is made to a combination of two essential components. One of these components (in free-base form) is urapidil. The other (in free form) is furosemide. Furosemide is in free form whenever the carboxyl group is in -COOH form; Urapidil is in free-base form when it is not in the form of an acid-addition salt.

What is claimed is:

1. A first component which, in free-base form, is urapidil in combination with a second component which, in free form, is furosemide; the proportion of the second component being sufficient to increase the effectiveness of the first as a hypotensive agent and the combination of the two components being physiologically active and pharmacologically-acceptable.

2. A combination according to claim 1 wherein the molar ratio of the first component to the second component is from 5:1 to 1:5.

3. A combination according to claim 1 wherein the second component is chemically combined with the first component.

4. A combination according to claim 3 in the form of the 1:1 furosemide acid-addition salt of urapidil.

5. A combination according to claim 1 wherein the molar ratio of the first component to the second component is from 3:1 to 1:3.

6. A physical combination according to claim 1 wherein the molar ratio of the first component to the second component is 1:1.

7. A combination according to claim 2 comprising a physical admixture of furosemide with urapidil.

8. A blood-pressure reducing medicament for subjects afflicted with hypertension and which comprises an effective concentration of a combination according to claim 1 and suitable diluent or excipient.

9. Medicament according to claim 8 in unit dosage form.

10. A pharmacologically-acceptable composition having a physiologically-active component and at least one component which is essentially therapeutically inactive, the active component comprising an effective concentration of a combination according to claim 1.

11. A process which comprises administering to a mammal afflicted with hypertension a blood-pressure-reducing amount of a combination according to claim 1.

12. A process according to claim 11 wherein the mammal is a human.

13. A process for reducing the toxicity of urapidil which comprises combining therewith a toxicity-reducing amount of furosemide.

14. A process according to claim 13 which comprises physically combining furosemide with urapidil in a form in which the two are not chemically combined.

15. A process according to claim 13 which comprises chemically combining furosemide with urapidil.

* * * * *